United States Patent
Nakamura

(10) Patent No.: US 10,980,518 B2
(45) Date of Patent: Apr. 20, 2021

(54) MEDICAL IMAGE CAPTURING CONTROL DEVICE, METHOD, AND PROGRAM

(71) Applicant: FUJIFILM Corporation, Tokyo (JP)

(72) Inventor: Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 412 days.

(21) Appl. No.: 15/868,626

(22) Filed: Jan. 11, 2018

(65) Prior Publication Data

US 2018/0256135 A1 Sep. 13, 2018

(30) Foreign Application Priority Data

Mar. 9, 2017 (JP) .............................. JP2017-044723

(51) Int. Cl.
*A61B 8/00* (2006.01)
*G06T 7/00* (2017.01)

(52) U.S. Cl.
CPC ................ *A61B 8/54* (2013.01); *A61B 8/469* (2013.01); *A61B 8/56* (2013.01); *G06T 7/0012* (2013.01); *A61B 8/58* (2013.01); *G06T 2207/10132* (2013.01); *G06T 2207/30048* (2013.01); *G06T 2207/30056* (2013.01)

(58) Field of Classification Search
CPC .. A61B 8/54; A61B 8/56; A61B 8/469; A61B 8/58; G06T 7/0012; G06T 2207/30048; G06T 2207/10132; G06T 2207/30056
See application file for complete search history.

(56) References Cited

U.S. PATENT DOCUMENTS

| 8,150,498 B2 * | 4/2012 | Gielen | G06T 7/73 600/427 |
| 8,320,711 B2 * | 11/2012 | Altmann | A61B 5/06 382/294 |
| 9,280,818 B2 * | 3/2016 | Fukatsu | G06K 9/6202 |

(Continued)

FOREIGN PATENT DOCUMENTS

| JP | 2000-300557 A | 10/2000 |
| JP | 2005-288043 A | 10/2005 |

(Continued)

OTHER PUBLICATIONS

Japanese Office Action for corresponding Japanese Application No. 2017-044723, dated Dec. 17, 2019, with an English translation.

(Continued)

*Primary Examiner* — Sanjay Cattungal
(74) *Attorney, Agent, or Firm* — Birch, Stewart, Kolasch & Birch, LLP

(57) ABSTRACT

A first determination unit performs first determination as to whether or not to store ultrasound images acquired in time series. In a case where the first determination is positive, a storage control unit stores ultrasound images, which are determined to be stored by the first determination unit, in a storage. A second determination unit performs second determination as to whether or not one or more ultrasound images to be stored are stored in the storage. In a case where the second determination is negative, a notification unit notifies that the one or more ultrasound images to be stored are not stored in the storage.

8 Claims, 3 Drawing Sheets

(56) References Cited

U.S. PATENT DOCUMENTS

| | | | | |
|---|---|---|---|---|
| 2008/0112627 A1* | 5/2008 | Oda | .................... | A61B 1/0005 |
| | | | | 382/232 |
| 2010/0063977 A1* | 3/2010 | Weese | ................... | G06F 19/321 |
| | | | | 707/769 |
| 2011/0019886 A1* | 1/2011 | Mizuno | ................. | G06T 7/0014 |
| | | | | 382/128 |
| 2015/0302605 A1* | 10/2015 | Sasaki | .................... | A61B 6/467 |
| | | | | 382/128 |

FOREIGN PATENT DOCUMENTS

| | | |
|---|---|---|
| JP | 2009-77960 A | 4/2009 |
| JP | 2012-24132 A | 2/2012 |
| JP | 2015-211831 A | 11/2015 |
| JP | 2016-85715 A | 5/2016 |

OTHER PUBLICATIONS

General Incorporated Foundation Japanese Society of of Sonographers e-learning [on-line], Mar. 19, 2015, Url: http://www.jss.org/e-learning/scanning/shinzou.html, 3 pages total.

Japanese Office Action dated Mar. 10, 2020, for Japanese Patent Application No. 2017-044723, with English translation.

* cited by examiner

MEDICAL IMAGE CAPTURING CONTROL DEVICE, METHOD, AND PROGRAM

CROSS REFERENCE TO RELATED APPLICATIONS

The present application claims priority under 35 U.S.C. § 119 to Japanese Patent Application No. 2017-044723 filed on Mar. 9, 2017. The above application is hereby expressly incorporated by reference, in its entirety, into the present application.

BACKGROUND

Field of the Invention

The present invention relates to a medical image capturing control device, method, and program for controlling the capturing of a medical image, such as an ultrasound image.

Description of the Related Art

Image diagnosis using medical images obtained by capturing a radiographic image and an ultrasound image of a patient has been performed. In addition, due to advances in medical apparatuses such as computed tomography (CT) apparatuses and MRI apparatuses, high-quality three-dimensional images with high resolution are used for image diagnosis.

On the other hand, with the recent aging of population, home healthcare is regarded important. However, in home healthcare, it is not possible to perform imaging using a CT apparatus and an MRI apparatus as described above. Therefore, the acquisition of a medical image using a compact and portable ultrasound apparatus is the key to image diagnosis in home healthcare. In home healthcare, using a portable ultrasound apparatus, a photographer displays an ultrasound image while moving an ultrasound probe so as to achieve appropriate positioning, and gives an instruction to store an image at the point in time of positioning at which a desired anatomical region is included, that is, a point in time at which a desired anatomical region is included in the ultrasound image, so that the ultrasound image including the desired anatomical region is stored.

In home healthcare, however, a person who captures a medical image is not a radiological technician accustomed to imaging but a doctor or a nurse unfamiliar with imaging in many cases. For this reason, it is often difficult to move the ultrasound probe so that appropriate positioning for acquiring an ultrasound image including a desired anatomical feature is achieved.

Therefore, a method of automatically storing a desired ultrasound image has been proposed. For example, JP2012-024132A has proposed a method in which, in the case of capturing an ultrasound image using a contrast medium, one or a plurality of ultrasound images having a brightness equal to or higher than a threshold value are selected as storage images and the selected ultrasound images are stored. JP2015-211831A has proposed a method of automatically storing ultrasound images of frames temporally before and after a desired ultrasound image. As described above, by using the methods disclosed in JP2012-024132A and JP2015-211831A, it is possible to automatically store a required ultrasound image while capturing an ultrasound image. As a result, it is possible to reduce the burden on the operator.

SUMMARY

On the other hand, depending on a part to be examined, ultrasound images according to a plurality of positioning may be required. In the methods disclosed in JP2012-024132A and JP2015-211831A, it is possible to automatically store ultrasound images. However, in order to check whether or not an ultrasound image to be stored can be stored, work such as displaying a stored ultrasound image is required. This increases the burden on the operator's work.

The invention has been made in view of the above circumstances, and it is an object of the invention to enable efficient storage of required medical images without omission.

A medical image capturing control device according to the invention comprises: first determination unit for performing first determination as to whether or not to store medical images acquired in time series by imaging unit; storage control unit for storing the medical images, which are determined to be stored, in storage unit in a case where the first determination is positive; second determination unit for performing second determination as to whether or not one or more medical images to be stored are stored in the storage unit; and notification unit for notifying that the one or more medical images to be stored are not stored in the storage unit in a case where the second determination is negative.

In the medical image capturing control device according to the invention, the first determination unit may perform the first determination based on an anatomical region included in each of the medical images.

In the medical image capturing control device according to the invention, in storing the plurality of medical images using a plurality of imaging procedures, in a case where the second determination is negative, the second determination unit may acquire information of an imaging procedure for a non-stored medical image. The notification unit may further send notification of the imaging procedure for the non-stored medical image.

The term "imaging procedure" is information indicating an imaging method and the positioning of imaging unit required to acquire a medical image that is to be stored, such as an imaging part, an imaging direction, and the contact position and direction of a probe in capturing an ultrasound image.

In the medical image capturing control device according to the invention, in storing the plurality of medical images for a plurality of parts of a subject, the storage control unit may store the one or more medical images to be stored in the storage unit for each of the parts.

In the medical image capturing control device according to the invention, the storage control unit may further store, in the storage unit, a plurality of medical images temporally before and after the one or more medical images to be stored.

In the medical image capturing control device according to the invention, the imaging unit may be ultrasound imaging unit.

In the medical image capturing control device according to the invention, the notification unit may further notify that the first determination is positive, and the storage control unit may store the medical images, which are determined to be stored and of which storage is instructed, in the storage unit.

A medical image capturing control method according to the invention comprises: performing first determination as to whether or not to store medical images acquired in time series by imaging unit; storing the medical images, which are determined to be stored, in storage unit in a case where the first determination is positive; performing second determination as to whether or not one or more medical images to be stored are stored in the storage unit; and notifying that the one or more medical images to be stored are not stored in the storage unit in a case where the second determination is negative.

In addition, a program causing a computer to execute the medical image capturing control method according to the present invention may be provided.

Another medical image capturing control device according to the invention comprises: a memory for storing a command to be executed by a computer; and a processor configured to execute the stored command. The processor executes: first determination processing for performing first determination as to whether or not to store medical images acquired in time series by imaging unit; storage control processing for storing the medical images, which are determined to be stored, in storage unit in a case where the first determination is positive; second determination processing for performing second determination as to whether or not one or more medical images to be stored are stored in the storage unit; and notification processing for notifying that the one or more medical images to be stored are not stored in the storage unit in a case where the second determination is negative.

According to the invention, the first determination as to whether or not to store the medical images acquired in time series is performed, and the medical images determined to be stored are stored in the storage unit in a case where the first determination is positive. In addition, the second determination as to whether or not one or more medical images to be stored are stored in the storage unit is performed, and notification indicating that the one or more medical images to be stored are not stored in the storage unit is sent in a case where the second determination is negative. For this reason, the operator can know that the medical images to be stored are not stored through the notification. Therefore, the medical image to be stored can be efficiently stored without omission.

DESCRIPTION OF THE PREFERRED EMBODIMENTS

Figure 1:
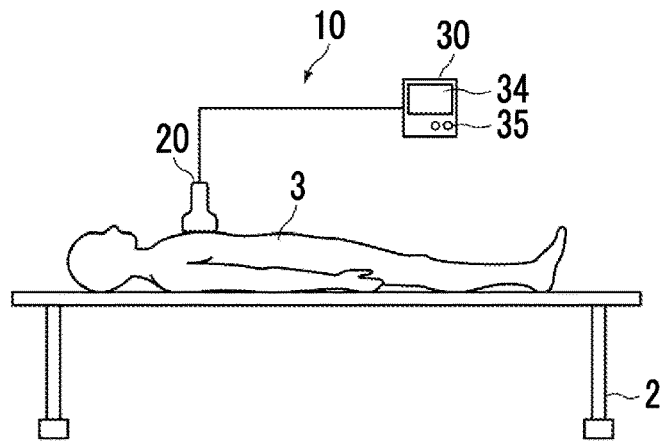
FIG. 1 is a schematic diagram of a medical image capturing system to which a medical image capturing control device according to an embodiment of the invention is applied.

Hereinafter, an embodiment of the invention will be described with reference to the accompanying diagrams. FIG. 1 is a schematic diagram of a medical image capturing system to which a medical image capturing control device according to the embodiment of the invention is applied. As shown in FIG. 1, the medical image capturing system according to the present embodiment is an apparatus for capturing an ultrasound image of a subject 3, and includes a portable ultrasound imaging apparatus 10.

The ultrasound imaging apparatus 10 includes an ultrasound probe (probe) 20 and an operating device 30 connected to the probe 20. The probe 20 and an imaging unit to be described later correspond to imaging unit, the operating device 30 is corresponds to a medical image capturing control device, and the ultrasound image corresponds to a medical image.

The probe 20 transmits an ultrasound wave toward the subject 3, receives an ultrasound wave reflected from the inside of the subject 3, and outputs a detection signal to the operating device 30.

The operating device 30 generates an ultrasound image based on the detection signal acquired by the probe 20. The operating device 30 includes a display 34 for displaying an ultrasound image and an input unit 35 for performing various inputs.

In the present embodiment, the operator moves the probe 20 on the surface of the subject 3 lying on a bed 2 to acquire an ultrasound image of the subject 3 at each moved position, and the acquired ultrasound image is displayed on the display 34 of the operating device 30 as a moving image.

The operating device 30 is realized by installing a medical image capturing control program of the invention on a computer mounted thereinside. The operating device 30 may be a dedicated device for acquiring an ultrasound image, but may be a portable notebook computer. The medical image capturing control program is distributed by being recorded on a recording medium, such as a digital versatile disc (DVD) or a compact disk read only memory (CD-ROM), and is installed onto the computer from the recording medium. Alternatively, the medical image capturing control program is stored in a storage device of a server computer connected to the network or in a network storage so as to be accessible from the outside, and is downloaded and installed onto the computer as necessary.

Figure 2:
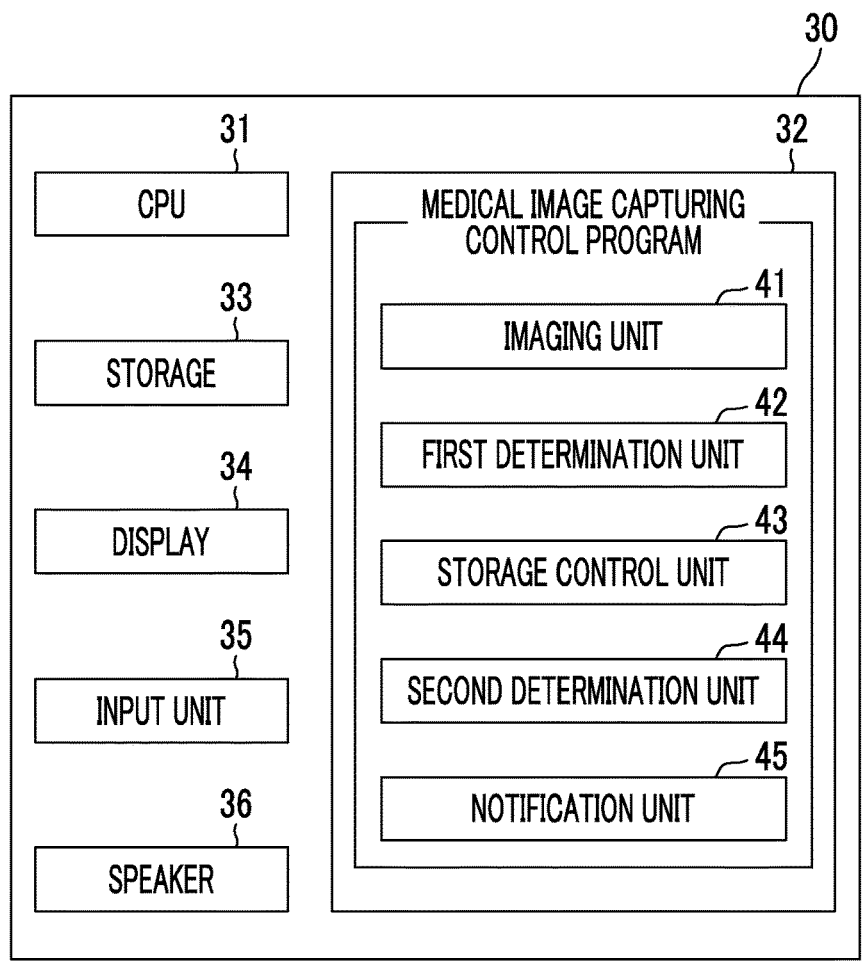
FIG. 2 is a diagram showing the schematic configuration of an operating device that is a medical image capturing control device realized by installing a medical image capturing control program according to the present embodiment on a computer.

FIG. 2 is a diagram showing the schematic configuration of an operating device that is a medical image capturing control device realized by installing the medical image capturing control program according to the present embodiment on a computer. As shown in FIG. 2, the operating device 30 includes a central processing unit (CPU) 31, a memory 32, a storage 33, the display 34, the input unit 35, and a speaker 36 as the configuration of a standard computer.

Various kinds of information including information required for processing and ultrasound images generated based on the detection signal acquired by the probe 20 are stored in the storage 33. In the present embodiment, a plurality of standard images to be described later are stored in the storage 33. In the present embodiment, it is assumed that ultrasound images of the heart and the liver of the subject 3 are acquired. The storage 33 corresponds to storage unit.

A medical image capturing control program is stored in the memory 32. As processing to be executed by the CPU 31, the medical image capturing control program defines imaging processing for imaging the detection signal input from the probe 20, first determination processing for performing first determination as to whether or not to store ultrasound images acquired in time series by the imaging processing, storage control processing of storing the ultrasound images, which are determined to be stored, in the storage 33 in a case where the first determination is positive, second determination processing for performing second determination as to whether or not one or more ultrasound images to be stored are stored in the storage 33, and notification processing for notifying that the one or more ultrasound images to be stored are not stored in the storage 33 in a case where the second determination is negative.

The CPU 31 executes these processes according to the program, so that the computer functions as an imaging unit 41, a first determination unit 42, a storage control unit 43, a second determination unit 44, and a notification unit 45. The operating device 30 may include a plurality of processors or processing circuits that perform imaging processing, first determination processing, storage control processing, second determination processing, and notification processing. The medical image capturing control device according to the present embodiment may not include the imaging unit 41.

The imaging unit 41 images the detection signal input from the probe 20 at a predetermined frame rate (for example, 30 fps) to sequentially acquire ultrasound images.

The first determination unit 42 performs first determination as to whether or not to store the ultrasound images acquired in time series by the imaging unit 41. For this reason, the first determination unit 42 acquires a standard image, which serves as a reference for performing the first determination, from the storage 33. In the present embodiment, ultrasound images of the heart and the liver are acquired. For diagnosis using ultrasound images, it is necessary to store a plurality of ultrasound images of a cross section including an anatomical region required for diagnosis for each of the heart and the liver.

Figure 3:
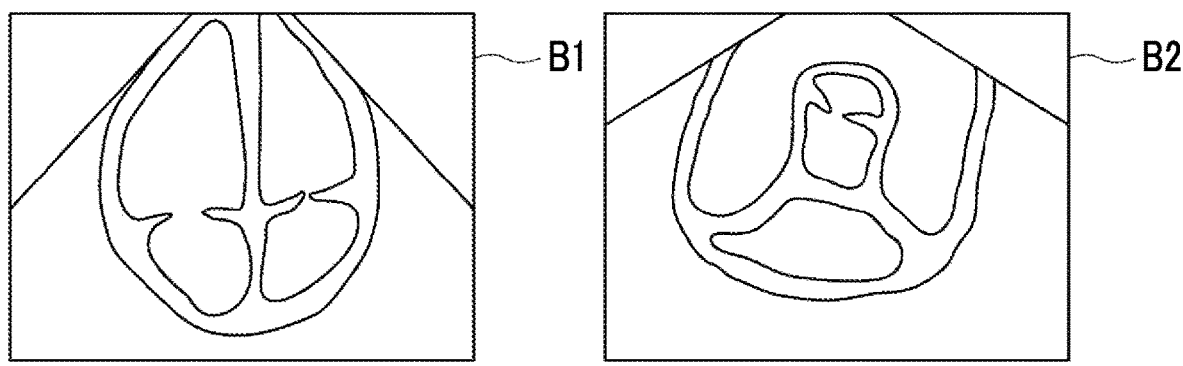
FIG. 3 is a diagram showing a standard image of the heart.

For example, for the heart, an ultrasound image including four chambers of the heart, that is, the left atrium, the left ventricle, the right atrium, and the right ventricle, an ultrasound image including the aortic valve, and the like are required. Therefore, for the heart, the first determination unit 42 acquires a standard image B1 including the left atrium, the left ventricle, the right atrium, and the right ventricle as anatomical regions, a standard image B2 including the aortic valve as an anatomical region, and the like from the storage 33, as shown in FIG. 3.

Figure 4:
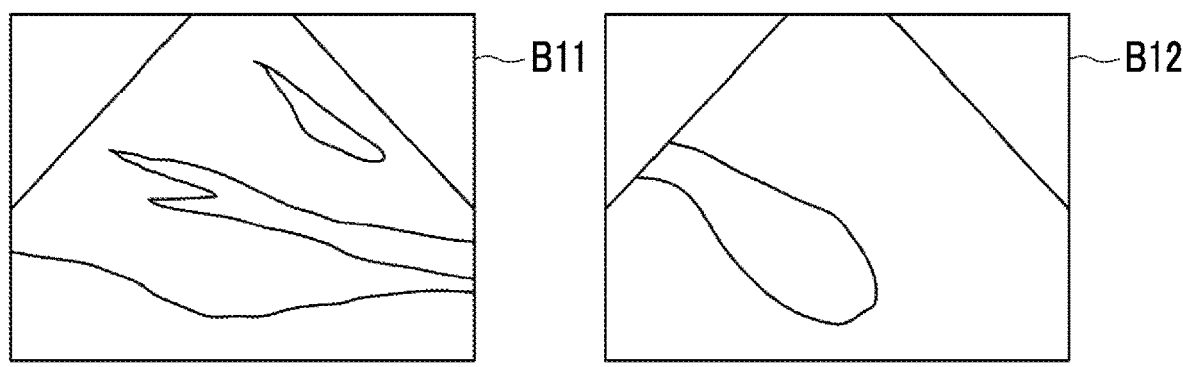
FIG. 4 is a diagram showing a standard image of the liver.

For the liver, an ultrasound image including the hepatic vein, an ultrasound image including the gallbladder, and the like are required. Therefore, for the liver, the first determination unit 42 acquires a standard image B11 including the hepatic vein as an anatomical region, a standard image B12 including the gallbladder as an anatomical region, and the like from the storage 33, as shown in FIG. 4.

In order to acquire ultrasound images corresponding to the acquired standard images, an imaging procedure including the contact position of the probe 20 and the direction of the probe 20 is defined. That is, an imaging procedure necessary for acquiring ultrasound images including anatomical features included in the standard images is defined for each of the standard images. In the present embodiment, it is assumed that, for each standard image stored in the storage 33, information of an imaging procedure for acquiring an ultrasound image corresponding to the standard image is given.

The operator captures an ultrasound image while changing the contact position and direction of the probe 20 on the surface of the subject 3 by using an imaging procedure for acquiring the ultrasound image corresponding to the acquired standard image. As a result, an ultrasound image including an anatomical region corresponding to the contact position and direction of the probe 20 is sequentially acquired at a predetermined frame rate by the imaging unit 41.

The first determination unit 42 calculates a correlation value between the ultrasound image and the standard image in order to perform first determination. As the correlation value, it is possible to use an inverse number of an absolute value of a difference between corresponding pixels and a value obtained by squaring a difference between pixels in the ultrasound image and the standard image. Then, in a case where the correlation value exceeds the threshold value, the first determination unit 42 determines that the ultrasound image for which the correlation value has been calculated is to be stored. For example, a correlation value is sequentially calculated for the ultrasound image that is sequentially acquired while making the probe 20 in contact with the vicinity of the heart of the subject 3 and changing the direction. Then, in a case where four chambers of the heart are included in the acquired ultrasound image, a correlation value between the ultrasound image and the standard image B1 shown in FIG. 3 increases to exceed the threshold value. In this case, the first determination unit 42 determines that the acquired ultrasound image is to be stored. In a case where there are a plurality of ultrasound images having correlation values exceeding the threshold value, a plurality of ultrasound images having high correlation values may be displayed on the display 34, so that the operator selects an ultrasound image to be stored.

In a case where the first determination of the first determination unit 42 is positive, the storage control unit 43 stores the ultrasound image, which is determined to be stored, in the storage 33. In the present embodiment, ultrasound images of the heart and the liver are acquired. Therefore, the storage control unit 43 stores an ultrasound image for each part in the storage 33. That is, a folder for the heart and a folder for the liver are generated in the storage 33, and the ultrasound image of the heart is stored in the folder for the heart and the ultrasound image of the liver is stored in the folder for the liver. For the standard image corresponding to the stored ultrasound image, a storage completion flag is assigned by the first determination unit 42.

The second determination unit 44 performs second determination as to whether or not one or more ultrasound images to be stored are stored in the storage 33. For example, it is assumed that ultrasound image storage using four imaging procedures is necessary for the heart and ultrasound image storage using four imaging procedures is necessary for the liver. The second determination unit 44 checks the flag of the standard image acquired by the first determination unit 42, and determines whether or not a storage completion flag is assigned to the standard image to be stored, thereby performing second determination as to whether or not the ultrasound image is stored in the storage 33.

In a case where the second determination is negative, the second determination unit 44 acquires an imaging procedure for a non-stored ultrasound image. Specifically, the first determination unit 42 acquires information of an imaging procedure associated with a standard image to which no flag is assigned. The acquired imaging procedure information is input to the notification unit 45.

Figure 5:
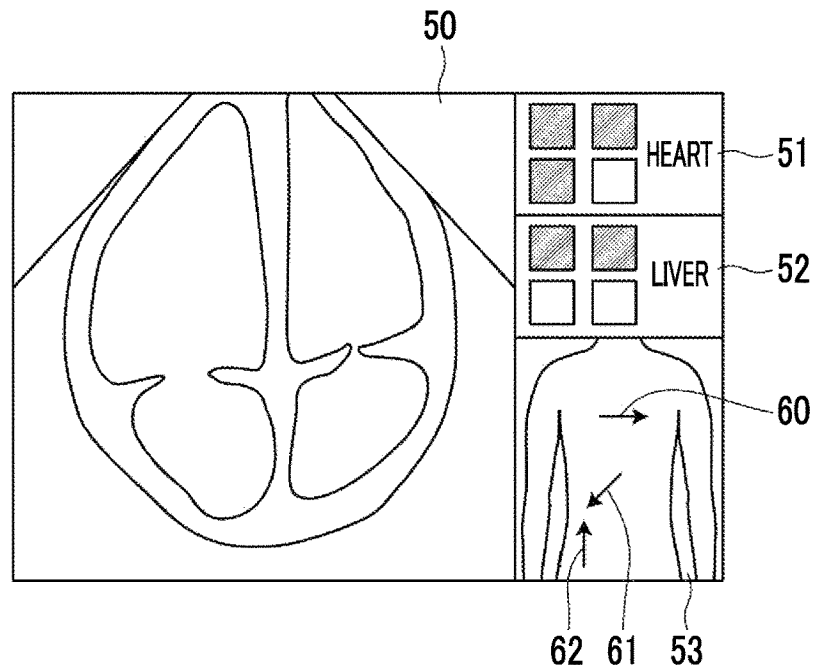
FIG. 5 is a diagram showing an example of notification.

In a case where the second determination is negative, the notification unit 45 notifies that an ultrasound image to be stored is not stored in the storage 33. Specifically, the notification unit 45 notifies the display 34 of the operating device 30 that an ultrasound image to be stored is not stored in the storage 33. FIG. 5 is a diagram showing an example of notification indicating that an ultrasound image to be stored is not stored in the storage 33. As shown in FIG. 5, an ultrasound image 50 being acquired, a list 51 of thumbnail images of standard images corresponding to ultrasound images to be stored for the heart, a list 52 of thumbnail images of standard image corresponding to ultrasound images to be stored for the liver, and a schema 53 that is an image of the body are displayed on the display 34. The part names of "heart" and "liver" are displayed in the lists 51 and 52, respectively. The notification unit 45 checks the flag of the standard image acquired by the first determination unit 42, and lowers the brightness of the thumbnail image of the standard image having the flag assigned thereto, that is, stored in the storage 33. In FIG. 5, in the thumbnail image list 51 of the heart, the brightness of three thumbnail images among the four thumbnail images is lowered. Therefore, it can be seen that three ultrasound images are stored. In FIG. 5, in the thumbnail image list 52 of the liver, the brightness of two thumbnail images among the four thumbnail images to be stored is lowered. Therefore, it can be seen that two ultrasound images are stored.

In the schema 53, information of an imaging procedure associated with a non-stored standard image to which no flag is assigned is given. In FIG. 5, an arrow 60 showing the contact position and direction of the probe 20 for acquiring the one remaining ultrasound image for the heart and arrows 61 and 62 showing the contact position and direction of the probe 20 for acquiring the two remaining ultrasound images for the liver are displayed.

By viewing the display 34, the operator can check whether or not there is a non-stored ultrasound image and an imaging procedure for acquiring the non-stored ultrasound image for each of the heart and the liver. Although the part names are displayed in the lists 51 and 52 to notify that an ultrasound image to be stored is not stored in the storage 33, an examination name or an examination purpose may be displayed for an operator, who is not familiar with the examination using an ultrasound apparatus, to notify that an ultrasound image to be stored is not stored in the storage 33.

In addition to or instead of the display on the display 34, the notification unit 45 may notify that an ultrasound image to be stored is not stored in the storage 33 by sound from the speaker 36. In this case, the notification unit 45 may only notify that all ultrasound images are not stored by sound, or may send notification of the imaging procedure for a non-stored ultrasound image, that is, the contact position and direction of the probe 20, by sound.

The notification unit 45 may display only the lists 51 and 52 of the thumbnail images of the standard images corresponding to the ultrasound images to be stored. Only the schema 53 may be displayed.

Figure 6:
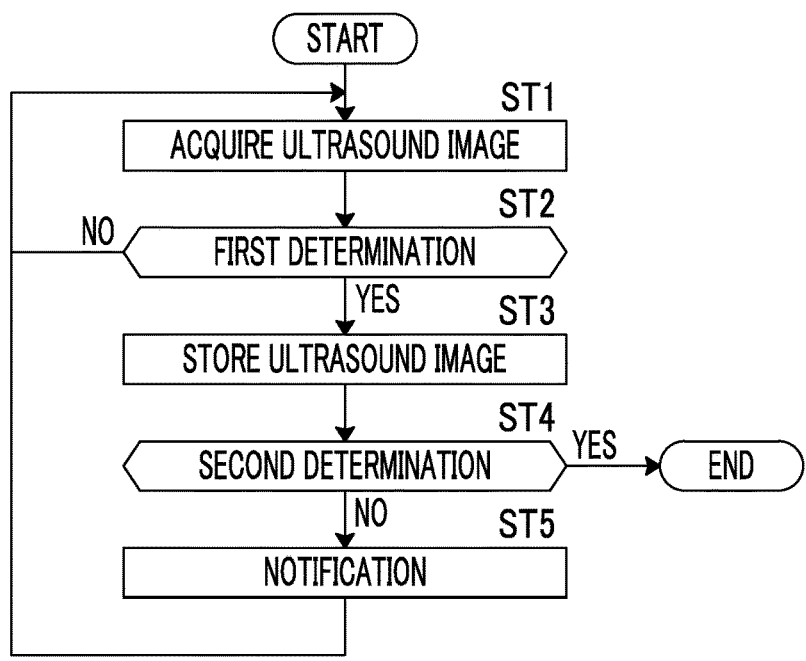
FIG. 6 is a flowchart showing a process performed in the present embodiment.

Next, a process performed in the present embodiment will be described. FIG. 6 is a flowchart showing the process performed in the present embodiment. In a case where an imaging instruction is given by the operating device 30, the imaging unit 41 images a detection signal input from the probe 20 to acquire an ultrasound image (step ST1). Then, the first determination unit 42 performs first determination as to whether or not to store the ultrasound images acquired in time series by imaging processing (step ST2). In a case where step ST2 is negative, the process returns to step ST1. In a case where step ST2 is positive, the storage control unit 43 stores the ultrasound image, which is determined to be stored by the first determination unit 42, in the storage 33 (step ST3).

Then, the second determination unit 44 performs second determination as to whether or not one or more ultrasound images to be stored are stored in the storage 33 (step ST4). In a case where step ST4 is negative, the notification unit 45 notifies that one or more ultrasound images to be stored are not stored in the storage 33 (step ST5), and the process returns to step ST1. In a case where step ST4 is positive, the process is ended.

As described above, in the present embodiment, the first determination as to whether or not to store the ultrasound image acquired in time series is performed, the second determination as to whether or not the ultrasound image to be stored is stored in the storage 33 is performed, and notification indicating that the ultrasound image to be stored is not stored in the storage 33 is sent in a case where the second determination is positive. For this reason, the operator can know that the ultrasound image to be stored is not stored by the notification. Therefore, the ultrasound image to be stored can be efficiently stored without omission.

In addition, by further notifying of an imaging procedure for a non-stored ultrasound image, the operator can know how to perform imaging for the non-stored ultrasound image. As a result, it is possible to easily acquire the non-stored ultrasound image.

In addition, by storing one or more ultrasound images, which need to be stored, in the storage 33 for each part, it becomes easy to refer to the stored ultrasound images for each part. Therefore, it is possible to efficiently perform diagnosis for each part by using the stored ultrasound images.

In the embodiment described above, only one ultrasound image is stored for one standard image. However, a plurality of ultrasound images temporally before and after the ultrasound image for which the first determination is positive may be stored in the storage 33. Therefore, it is also possible to refer to the ultrasound images in the vicinity of the required ultrasound image at the time of diagnosis. It is preferable that the number of ultrasound images to be stored is set in advance. The number of ultrasound images to be stored may be set for each part whose ultrasound image is to be acquired.

In the above embodiment, the first determination is performed based on the correlation value between the ultrasound image and the standard image. However, determination as to whether or not a predetermined anatomical region in an ultrasound image has been detected at a predetermined position may be performed as the first determination. For example, in a case where the ultrasound image including the four chambers of the heart is an ultrasound image to be stored, it is assumed that the first determination unit 42 has a discriminator for detecting the left atrium, the left ventricle, the right atrium, and the right ventricle. In the discriminator, machine learning is performed using the teacher data of the left atrium, the left ventricle, the right atrium, and the right ventricle. In this case, the first determination of the first determination unit 42 is positive in a case where the four chambers of the heart are detected at a predetermined position.

In the embodiment described above, the storage control unit 43 automatically stores the ultrasound image in the storage 33 in a case where the first determination is positive. However, in a case where the first determination is positive, the notification unit 45 may send notification of the fact, and the operator may operate the input unit 35 based on the notification to store the ultrasound image in the storage 33 by manual operation.

In the embodiment described above, notification indicating that the ultrasound image to be stored is not stored in the storage 33 is sent at the timing during the imaging. However, the notification indicating that the ultrasound image to be stored is not stored in the storage 33 may be sent at the timing at which the operator gives an instruction to end the imaging or the examination in the operating device 30.

In addition, although the ultrasound image is used as a medical image in the embodiment described above, it is needless to say that a radiographic image may be used.

Hereinafter, the effect of the present embodiment will be described.

The operator can know how to perform imaging for a non-stored medical image by acquiring the information of an imaging procedure for the non-stored medical image and further notifying of the imaging procedure for the non-stored medical image. As a result, it is possible to easily acquire the non-stored medical image.

In the case of storing a plurality of medical images for a plurality of parts of the subject, by storing one or more medical images to be stored in storage unit for each part, it becomes easy to refer to the stored medical images for each part. Therefore, it is possible to efficiently perform diagnosis for each part by using the stored medical images.

By further storing a plurality of medical images temporally before and after one or more medical images to be stored, medical images in the vicinity of the medical image to be stored can also be referred to at the time of diagnosis.

What is claimed is:

1. A medical image capturing control device, comprising a processor configured to:
    perform a first determination as to whether or not to store medical images acquired in time series by a probe;
    store the medical images, which are determined to be stored, in a storage in a case where the first determination is positive;
    perform a second determination as to whether or not one or more medical images to be stored are stored in the storage; and
    notify that the one or more medical images to be stored are not stored in the storage in a case where the second determination is negative,
    wherein, in storing a plurality of the medical images using a plurality of imaging procedures, in a case where the second determination is negative, the processor is further configured to:
        acquire information of an imaging procedure for a non-stored medical image among the plurality of imaging procedures; and
        provide notification regarding the imaging procedure for the non-stored medical image.

2. The medical image capturing control device according to claim 1,
    wherein the processor is further configured to perform the first determination based on an anatomical region included in each of the medical images.

3. The medical image capturing control device according to claim 1,
    wherein, in storing a plurality of medical images for a plurality of parts of a subject, the processor is further configured to store the one or more medical images to be stored in the storage for each of the parts.

4. The medical image capturing control device according to claim 1,
    wherein the processor is further configured to store, in the storage, a plurality of medical images temporally before and after the one or more medical images to be stored.

5. The medical image capturing control device according to claim 1,
    wherein the probe is an ultrasound probe.

6. The medical image capturing control device according to claim 1,
    wherein the processor is further configured to notify that the first determination is positive, and store the medical images, which are determined to be stored and of which storage is instructed, in the storage.

7. A medical image capturing control method, comprising:
    performing a first determination as to whether or not to store medical images acquired in time series by a probe;
    storing the medical images, which are determined to be stored, in a storage in a case where the first determination is positive;
    performing a second determination as to whether or not one or more medical images to be stored are stored in the storage; and
    notifying that the one or more medical images to be stored are not stored in the storage in a case where the second determination is negative,
    wherein, in storing a plurality of the medical images using a plurality of imaging procedures, in a case where the second determination is negative, the method further comprises:
        acquiring information of an imaging procedure for a non-stored medical image among the plurality of imaging procedures; and
        providing notification regarding the imaging procedure for the non-stored medical image.

8. A non-transitory computer-readable recording medium having stored therein a medical image capturing control program causing a computer to execute:
    a step of performing a first determination as to whether or not to store medical images acquired in time series by a probe;
    a step of storing the medical images, which are determined to be stored, in a storage in a case where the first determination is positive;
    a step of performing a second determination as to whether or not one or more medical images to be stored are stored in the storage; and
    a step of notifying that the one or more medical images to be stored are not stored in the storage in a case where the second determination is negative,
    wherein, in storing a plurality of the medical images using a plurality of imaging procedures, in a case where the second determination is negative, the computer further executes:
        a step of acquiring information of an imaging procedure for a non-stored medical image among the plurality of imaging procedures; and
        a step of providing notification regarding the imaging procedure for the non-stored medical image.

* * * * *